US009084590B2

(12) United States Patent
Wittenberger et al.

(10) Patent No.: US 9,084,590 B2
(45) Date of Patent: Jul. 21, 2015

(54) DEVICE AND METHOD FOR IMPROVED SAFETY AND EFFICACY FOR CRYOABLATION

(71) Applicant: MEDTRONIC CRYOCATH LP, Toronto (CA)

(72) Inventors: Dan Wittenberger, L'Île-Bizard (CA); Rachid Mahrouche, Lasalle (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 141 days.

(21) Appl. No.: 13/803,450

(22) Filed: Mar. 14, 2013

(65) Prior Publication Data

US 2014/0276710 A1    Sep. 18, 2014

(51) Int. Cl.
*A61B 18/02*    (2006.01)
*A61B 18/00*    (2006.01)

(52) U.S. Cl.
CPC ....... *A61B 18/02* (2013.01); *A61B 2018/00041* (2013.01); *A61B 2018/00577* (2013.01); *A61B 2018/00744* (2013.01); *A61B 2018/00791* (2013.01); *A61B 2018/00863* (2013.01); *A61B 2018/0212* (2013.01)

(58) Field of Classification Search
USPC .................................................... 606/21, 27
See application file for complete search history.

(56) References Cited

U.S. PATENT DOCUMENTS

| 5,452,582 A | 9/1995 | Longsworth |
| 5,522,870 A | 6/1996 | Ben-Zion |
| 2011/0092967 A1 | 4/2011 | Harvey-Poncelet et al. |
| 2011/0152849 A1* | 6/2011 | Baust et al. ..................... 606/21 |

OTHER PUBLICATIONS

International Search Report and Written Opinion dated May 30, 2014 International Application Serial No. PCT/CA2014/000187, International Filing Date: Mar. 7, 2014 consisting of 8 pages.

* cited by examiner

*Primary Examiner* — Nicole F Lavert
(74) *Attorney, Agent, or Firm* — Christopher & Weisberg, P.A.

(57) ABSTRACT

A method and system for improved lesion creation. The method generally includes positioning a treatment element of a medical device proximate an area of target tissue and operating a control unit in accordance with a duty cycle, that includes at least one freeze-warm cycle, each freeze-warm cycle including: supplying coolant to the treatment element at a first flow rate that causes the treatment element to reach a first temperature, the first temperature causing ablation of the target tissue and cryoadhesion between the treatment element and target tissue, and supplying coolant to the treatment element at a second flow rate that causes the treatment element to reach a second temperature, the second temperature being higher than the first temperature and the second flow rate being lower than the first flow rate, the second temperature being above a temperature at which ablation occurs and below a temperature at which cryoadhesion is broken.

21 Claims, 2 Drawing Sheets

DEVICE AND METHOD FOR IMPROVED SAFETY AND EFFICACY FOR CRYOABLATION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for cryoablation. Specifically, the present method and system provides effective cryoablation of tissue and enhances patient safety by reducing the need for fluoroscopy.

BACKGROUND OF THE INVENTION

Cryoablation, a therapy that uses that removal of heat from tissue, is often used to treat cardiac conditions such as cardiac arrhythmias. In most cryoablation procedures, a pressurized refrigerant is circulated within the tip of a cryoablation catheter, where the refrigerant expands and absorbs heat from surrounding tissue. As the tissue freezes, blood adjacent the treatment site may also freeze, creating an "ice ball" that temporarily adheres the treatment element (for example, a cryoballoon or thermally conductive area at the tip of the cryoablation device) to the tissue at the treatment site, a phenomenon called cryoadhesion.

Cryoadhesion is advantageous in that it helps prevent the cryoablation device from moving away from the target treatment site of a beating heart. However, research has shown that a freeze-thaw-freeze cycle more effectively ablates tissue than a single longer freeze-only cycle. Although more efficient lesion creation is desired, the freeze-thaw-freeze cycle may also result in the thawing of the ice ball that keeps the cryoablation device in place. As a result, the device must be repositioned, which may be complicated and time-consuming. Further, some cryoablation procedures, such pulmonary vein isolation (PVI), involve the use of fluoroscopy to visualize the position of the device and to make sure that, for example, the pulmonary vein is completely occluded. Fluoroscopy involves x-ray visualization; consequently, each time the ice ball thaws and the cryoablation device is repositioned, the patient and the user are exposed to an increased amount of radiation.

Therefore, it is desirable to provide a method and system for more efficient cryoablation, while reducing the need for fluoroscopy.

SUMMARY OF THE INVENTION

The present invention advantageously provides a method and system for improved lesion creation in tissue. In one embodiment, the method may generally include positioning a distal end of a medical device proximate an area of target tissue, and operating a control unit according to a treatment cycle. The treatment cycle may include supplying coolant to the distal portion of the medical device at a first flow rate, the first flow rate causing the distal portion of the medical device to reach a first temperature, and supplying coolant to the distal portion of the medical device at a second flow rate, the second flow rate causing the distal portion of the medical device to reach a second temperature, the second temperature being higher than the first temperature and the second flow rate being lower than the first flow rate. The first temperature being sufficiently low so as to ablate the target tissue and cause cryoadhesion between the distal portion of the medical device and the target tissue, the second temperature being above a temperature at which ablation occurs and below a temperature at which cryoadhesion is broken. The treatment cycle may further include supplying coolant to the distal portion of the medical device at a third flow rate, the third flow rate causing the distal portion of the medical device to reach a third temperature, the third temperature being higher than the first temperature but lower than the second temperature, and the third flow rate being lower than the first flow rate but higher than the second flow rate, and supplying coolant to the distal portion of the medical device at a fourth flow rate, the fourth flow rate causing the distal portion of the medical device to reach a fourth temperature, the fourth temperature being higher than the first and third temperatures but lower than the second temperature, and the fourth flow rate being higher than the second flow rate but lower than the first and third flow rates. The third temperature may be sufficiently low so as to ablate the target tissue and cause cryoadhesion between the distal portion of the medical device and the target tissue, the fourth temperature being above a temperature at which ablation occurs and below a temperature at which cryoadhesion is broken. For example, the first temperature may be between approximately $-50°$ C. to approximately $-70°$ C.; the first flow rate may be between approximately 7000 and 7500 standard cubic centimeters per minute (sccm); the second temperature may be between approximately $-15°$ C. and approximately $-5°$ C.; the second flow rate may be between approximately 3500 sccm and approximately 3000 sccm; the third temperature may be between approximately $-35°$ C. to approximately $-40°$ C.; the third flow rate may be between approximately 4500 sccm to approximately 5000 sccm; the fourth temperature may be between approximately $-15°$ C. and approximately $-20°$ C.; and the fourth flow rate may be between approximately 4000 sccm and approximately 4200 sccm. The coolant may be continuously delivered to a distal portion of the medical device.

In another embodiment, the method may generally include positioning a treatment element coupled to the distal end of a medical device proximate an area of target tissue, and operating a control unit in accordance with a duty cycle, the control unit being in communication with the treatment element, the duty cycle including at least one freeze-warm cycle, each freeze-warm cycle including: supplying coolant to the treatment element at a first flow rate, the first flow rate causing the treatment element to reach a first temperature, the first temperature causing ablation of the target tissue and causing cryoadhesion between the treatment element and target tissue, and supplying coolant to the treatment element at a second flow rate, the second flow rate causing the treatment element to reach a second temperature, the second temperature being higher than the first temperature and the second flow rate being lower than the first flow rate, the second temperature being above a temperature at which ablation occurs and below a temperature at which cryoadhesion is broken. For example, the duty cycle may include two or more freeze-warm cycles.

The system may generally include a medical device including a distal portion defining a treatment element, a fluid supply in communication with the treatment element, the fluid supply continuously delivering fluid to the treatment element when the treatment element is activated, and a control unit having a processor, the processor operating to control the flow of fluid according to a duty cycle. The duty cycle may include: a freezing cycle over a first time interval during which the fluid flow rate is increased to lower the temperature of the treatment element to a first ablation temperature; a warming cycle over a second time interval during which the fluid flow rate is decreased to raise the temperature of the treatment element to a first maintenance temperature, the first maintenance temperature being higher than the first ablation temperature; a freezing cycle over a third time interval during which the fluid flow rate is increased to lower the temperature of the treatment element to a second ablation temperature, the second ablation temperature being higher than the first ablation temperature but lower than the first maintenance temperature; and a freezing cycle over a fourth time interval during which the fluid flow rate is decreased to raise the temperature of the treatment element to a second maintenance temperature, the second maintenance temperature being higher than the first ablation temperature but lower than the first maintenance temperature. For example, the first ablation temperature may be between approximately 50° C. to approximately −70° C. and the first flow rate may be between approximately 7000 and 7500 sccm; the first maintenance temperature may be between approximately −15° C. and approximately −5° C. and the first maintenance flow rate may be between approximately 3500 sccm and approximately 3000 sccm; the second ablation temperature may be between approximately −35° C. to approximately −40° C. and the second ablation flow rate may be between approximately 4500 sccm to approximately 5000 sccm; and the second maintenance temperature may be between approximately −15° C. and approximately −20° C. and the second maintenance flow rate may be between approximately 4000 sccm and approximately 4200 sccm.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
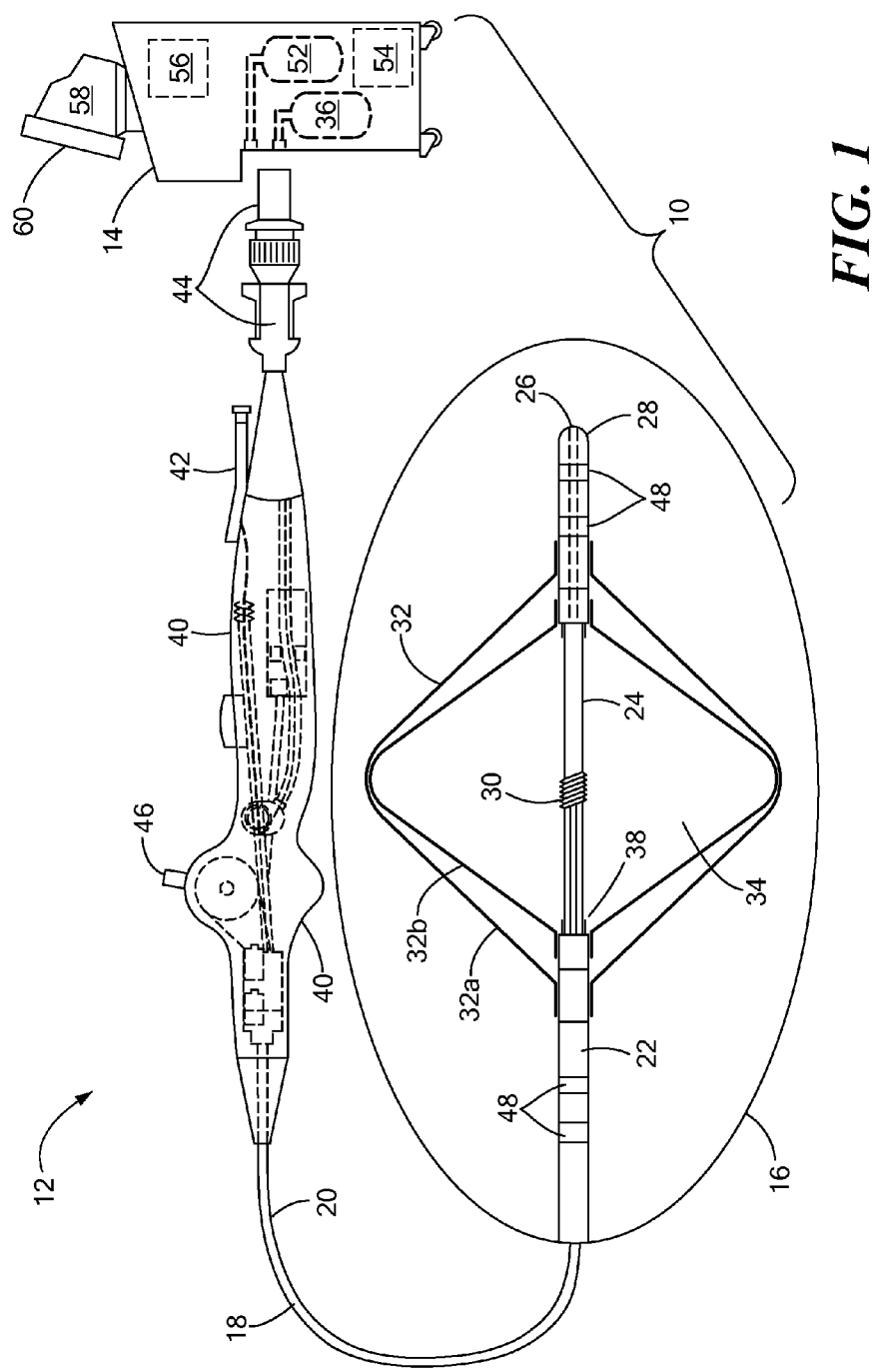
FIG. 1 shows an exemplary cryoablation system in accordance with the present invention, the system including a first embodiment of a distal end of a cryoablation device.

Referring now to the drawing figures in which like reference designations refer to like elements, an embodiment of a medical system constructed in accordance with principles of the present invention is shown in FIG. 1 and generally designated as "10." The system 10 may generally include a medical device 12 that may be coupled to a control unit 14 or operating console. The medical device 12 may generally include one or more treatment elements for cryotherapy and, optionally, other energy modalities. For example, the distal portion 16 of the device 12 may include one or more treatment elements may be configured to remove heat from tissue, thus being capable of cryotreatment or cryoablation, including of cardiac tissue. The device may further include one or more treatment elements configured to heat tissue to ablation or sub-ablation temperatures (for example, radiofrequency electrodes).

Figure 2:
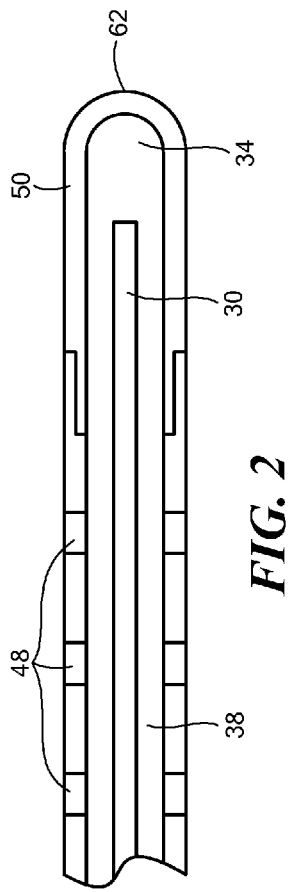
FIG. 2 shows cross-sectional view of a second embodiment of a distal end of a cryoablation device in accordance with the present invention.

It is noted that the one or more treatment elements and/or the distal portion 16 of the medical device 12 may define or assume a shape that is independent of the coolant flow. Although the shape of the distal portion 16 of a focal catheter (such as shown in FIG. 2) will generally be independent of coolant flow, treatment elements such as cryoballoons are often kept in an inflated or expanded configuration by the pressure and/or volume of the coolant that is circulated within. For example, many cryoablation systems use an initial fixed volume of fluid to inflate a cryoballoon before treatment begins. In such a system, a predetermined volume of fluid that is specific to the device being used may be delivered to an inflation reservoir from the fluid supply reservoir at room temperature or without being cooled. That is, the temperature is above cryoablation or even cryocooling temperatures. For example, the initial volume of fluid may have a temperature that is close to, or slightly above, room temperature. Once the initial volume is received within the inflation reservoir, a valve may be used to close the inflation reservoir from the fluid supply reservoir. Then, another valve may be used to open the fixed initial volume reservoir to the device, wherein the fixed initial volume inflates the cryoballoon to a predetermined inflation level. After the inflation phase is over, the system enters into a transition phase and then an ablation phase that includes a continuous flow of coolant at cryoablation temperatures. If a thawing phase is desired, the injection of coolant from the fluid supply reservoir is stopped altogether. If another ablation cycle is desired, the system is evacuated or flushed by using one or more valves to open the fluid flow path of the system to a vacuum. After evacuation, the inflation reservoir is refilled with fluid. During the refilling phase, the fluid flow path of the system is open to the vacuum.

Such fixed initial volume systems may only be used for a specific device, as the size of the inflation reservoir is predetermined, and cannot be adapted for use with, for example, a different type or size of device or newer generation of a device. Additionally, these systems are generally "on/off" and do not easily allow for temperature modification during an ablation procedure.

The system 10 described herein is a "continuous flow" system, rather than the "fixed initial volume" system described above. In this continuous flow system 10, the details of which are further shown and described in FIG. 3, the coolant flow rate may be adjusted upstream and/or downstream of the device 12 to allow the treatment element to reach sub-ablation temperatures without breaking cryoadhesion between the treatment element and target tissue. That is, the flow of coolant from the fluid supply reservoir 36 does not have to be completely shut off to allow for a warm cycle, and the warm cycle does not completely thaw the ice ball between the treatment element and tissue. Further, because the shape of the treatment element and/or the distal portion 16 of the device 12 is independent of coolant flow, the flow rate of the coolant both upstream and downstream of the device may be adjusted to adjust treatment element temperature without the risk of deflation (for example, if a cryoballoon is used).

Referring now to FIG. 1 in detail, the medical device 12 may include an elongate body 18 passable through a patient's vasculature and/or proximate to a tissue region for diagnosis or treatment, such as a catheter, sheath, or intravascular introducer. The elongate body 18 may define a proximal portion 20 and a distal portion 22, and may further include one or more lumens disposed within the elongate body 18 thereby providing mechanical, electrical, and/or fluid communication between the proximal portion 20 of the elongate body 18 and the distal portion 22 of the elongate body 18 (not shown).

The medical device 12 may include a shaft 24 at least partially disposed within a portion of the elongate body 18. The shaft 24 may extend or otherwise protrude from a distal end 22 of the elongate body 18, and may be movable with respect to the elongate body 18 in longitudinal and rotational directions. That is, the shaft 24 may be slidably and/or rotatably movable with respect to the elongate body 18. The shaft 24 may further define a lumen 26 therein for the introduction and passage of a guide wire (not shown). The shaft 24 may include or otherwise be coupled to a distal tip 28 that defines an opening and passage therethrough to the lumen 26 through which the guide wire may exit the distal tip 28 of the device 12.

The medical device 12 may further include a fluid delivery conduit 30 traversing at least a portion of the elongate body 18 and towards the distal portion 22 of the elongate body 18. The delivery conduit 30 may be coupled to or otherwise extend from the distal portion 22 of the elongate body 18, and/or may be coupled to a portion of the shaft 24 and/or distal tip 28 of the medical device 12. The fluid delivery conduit 30 may define a lumen therein for the passage or delivery of a fluid from the proximal portion of the elongate body 18 and/or the control unit 14 to the one or more treatment elements of the medical device 12. A distal portion of the fluid delivery conduit 30 may further include one or more apertures or openings therein, to provide for the dispersion or directed ejection of fluid from the lumen to an environment exterior to the fluid delivery conduit 30.

As shown in FIG. 1, the one or more treatment elements may be one or more expandable elements or balloons 32 at the distal portion 22 of the elongate body 18. For example, the medical device 12 may include a treatment element that includes one or more cryoballoons 32. As a non-limiting example, the medical device 12 of FIG. 1 includes an outer cryoballoon 32a and an inner cryoballoon 32b. At least a portion of each cryoballoon 32a, 32b may be coupled to a portion of the distal portion 22 of the elongate body 18 and at least a portion of each cryoballoon 32a, 32b may be coupled to a distal portion of the shaft 24 and/or distal tip 28 to define an interior chamber or region 34 within which a portion of the fluid delivery conduit 30 may be contained. For example, the inner cryoballoon 32b may define an interior chamber or region 34 that contains coolant or fluid dispersed from the fluid delivery conduit 30. The coolant may be delivered from a fluid supply reservoir 36 to the interior chamber 34 under pressure, such that the coolant expands within the interior chamber 34 upon exiting the fluid delivery conduit 30. This expansion causes a decrease in the temperature of the coolant, and therefore of the one or more cryoballoons 32, to ablation and/or sub-ablation temperatures via the Joule-Thompson effect. The interior chamber 34 may also be in fluid communication with a fluid exhaust conduit 38 defined by or included in the elongate body 18 for the removal of expanded coolant from the interior chamber 34 of the cryoballoon 32 (for example, the inner cryoballoon 32b as shown in FIG. 1). The cryoballoon 32 may further include one or more material layers providing for puncture resistance, radiopacity, or the like. Further, each cryoballoon may be either substantially compliant or substantially noncompliant. Although two cryoballoons 32a, 32b are shown in FIG. 1, it will be understood that any number and/or configuration of expandable elements may be used, and that the one or more treatment elements may include expandable elements other than cryoballoons.

The medical device 12 may include a handle 40 coupled to the proximal portion 20 of the elongate body 18. The handle 40 can include circuitry for identification and/or use in controlling of the medical device 12 or another component of the system 10. Additionally, the handle 40 may be provided with a fitting 42 for receiving a guide wire that may be passed into the guide wire lumen 26. The handle 40 may also include one or more connectors 44 that are matable to the control unit 14 to establish communication between the medical device 12 and one or more components or portions of the control unit 14. The handle 40 may also include one or more actuators or control mechanisms that allow a user to control, deflect, steer, or otherwise manipulate a distal portion 22 of the medical device 12 from the proximal portion 20 of the medical device 12. For example, the handle 40 may include one or more components such as steering elements (for example, a lever or knob 46) for manipulating the elongate body 18 and/or additional components of the medical device 12. For example, a pull wire for steering the distal portion 22 of the elongate body 18 may be anchored at its proximal end to a portion of the handle 40 in communication with one or more steering elements 46.

Continuing to refer to FIG. 1, the medical device 12 may further include one or more conductive segments or mapping electrodes 48 positioned on or about the elongate body 18 for measuring, recording, or otherwise assessing one or more electrical properties or characteristics of surrounding tissue. For example, mapping electrodes 48 may be used for recording electrocardiogram or monophasic action potential (MAP) signals. Additionally, the medical device 12 may include one or more conductive segments or treatment electrodes 50 conveying an electrical signal, current, or voltage to a designated tissue region (for example, as shown in FIG. 2). The electrodes 48, 50 may be configured in a myriad of different geometric configurations or controllably deployable shapes, and may also vary in number to suit a particular application, targeted tissue structure or physiological feature. In the non-limiting example shown in FIG. 1, the medical device 12 may include a first pair of mapping electrodes 48 proximal to the cryoballoons 32a, 32b and a second pair of mapping electrodes 48 distal to the cryoballoons 32a, 32b.

Continuing to refer to FIG. 1, the system 10 may include one or more fluid reservoirs, such as a fluid supply reservoir 36 and a fluid return reservoir 52. For example, the fluid supply reservoir 36 and/or fluid return reservoir 52 may be located within the control unit or console 14. The fluid supply reservoir 36 may be in fluid communication with the fluid delivery conduit 30, and the fluid return reservoir 52 may be in fluid communication with the fluid exhaust conduit 38, and may be in communication with an exhaust or scavenging system (not shown) for recovering or venting expended fluid for re-use or disposal, as well as various control mechanisms and a vacuum pump 54. The vacuum pump 54 may create a low-pressure environment in one or more conduits or lumens within the medical device 12 (such as the fluid exhaust conduit 38) so that expanded fluid is drawn into the lumen of the elongate body 18 from, for example, the interior chamber 34, towards the proximal portion 20 of the elongate body 18. In addition to providing an exhaust function for the fluid or coolant supply reservoir 36, the control unit 14 may also include pumps, valves, controllers or the like to recover and/or re-circulate fluid delivered to the handle 40, the elongate body 18, and/or the fluid pathways of the medical device 12.

The system 10 may further include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/ fluid paths of the medical device 12. Such valves, controllers, or the like may be located in a portion of the medical device 12 and/or in the control unit 14. For example, each electrode 48, 50 may include a sensor, such as a thermocouple, an electrical conductivity sensor, a spectrometer, a pressure sensor, a fluid flow sensor, a pH sensor, and/or a thermal sensor (not shown) coupled to or in communication with the electrodes 48, 50. The sensors may also be in communication with a feedback portion of the control unit 14 to trigger or actuate changes in operation when predetermined sequences, properties, or measurements are attained or exceeded.

Continuing to refer to FIG. 1, the control unit 14 may additionally include an energy generator or power source 56 as a treatment or diagnostic mechanism in communication with the electrodes 48, 50 of the medical device 12. For example, the control unit 14 may include a radiofrequency (RF) generator 56 for providing RF energy delivery in addition to cryotreatment functionality. Additionally or alternatively, energy may be used for pacing myocardial cells in a mapping procedure. The radiofrequency generator 56 may have a plurality of output channels, with each channel coupled to an individual electrode 48, 50. For example, if RF treatment is used in addition to cryotreatment, the radiofrequency generator 56 may be operable in one or more modes of operation, including for example bipolar energy delivery between at least two treatment electrodes 50 on the medical device 12 within a patient's body, monopolar or unipolar energy delivery to one or more of the electrodes 50 on the medical device 12 within a patient's body and through a patient return or ground electrode (not shown) spaced apart from the electrodes 50 of the medical device 12 (for example, on a patient's skin), and combinations thereof.

The control unit 14 may include one or more controllers, processors, and/or software modules containing instructions or algorithms (collectively referred to as "computers 58") to provide for the automated operation and performance of the features, sequences, calculations, or procedures described herein. For example, the control unit 14 may include a signal processing unit or computer 58 to measure one or more electrical characteristics between the electrodes 48, 50 of the medical device 12. An excitation current may be applied between one or more of the electrodes 48, 50 on the medical device 12 and/or a patient return electrode, and the resulting voltage, impedance, or other electrical properties of the target tissue region may be measured, for example, in an electrogram. Unipolar electrograms may be recorded with the mapping electrode 48 as the positive electrode, and another electrode on the body surface or remote from the field or cardiac excitation as the negative electrode. The control unit 14 may further include one or more displays or screens 60 to display the various recorded signals and measurement, for example, an electrogram.

Figure 3:
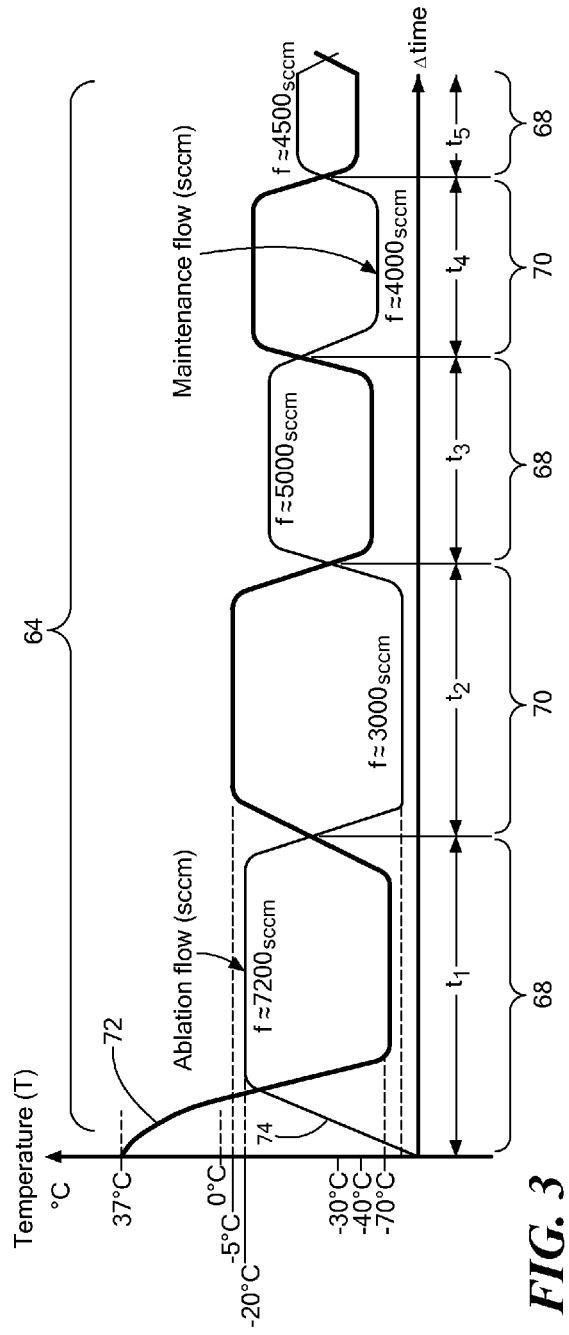
FIG. 3 shows a graphical representation of an exemplary cryoablation system duty cycle in accordance with the present invention.

As is shown and described in greater detail in FIG. 3, the one or more computers 58, controllers, processors, and/or software modules containing instructions or algorithms of the control unit 14 may be used for the automatic or manual control of coolant flow within the system according to a preferred duty cycle. Although the control unit 14 may be programmed to follow a predefined duty cycle, feedback signals from one or more system 10 components may allow for the duty cycle to be adjusted in real time in order to effectively ablate target tissue.

Referring now to FIG. 2, a second embodiment of a medical device 12 is shown. The medical device 12 may be configured for use with a system 10 such as that shown and described in FIG. 1. The device of FIG. 2 may have a fixed diameter (that is, may not include an expandable element or balloon 32, as in FIG. 1), such as a focal catheter. The one or more treatment elements may include one or more electrodes 48, 50 coupled directly to the distal portion 22 of the elongate body 18. In the non-limiting example of FIG. 2, the medical device 12 may include a treatment electrode 50 at the distal tip 62 and one or more mapping electrodes 48 in the distal portion 22 of the elongate body 18. Additionally, the treatment electrode 50 may also have mapping functionality. The electrodes 48, 50 may have any of a myriad of shapes, sizes, and configurations. As shown in FIG. 2, for example, the mapping electrodes 48 may be band electrodes and the treatment electrode 50 may be configured to fit about the distal tip 62 of the device 12.

The medical device 12 of FIG. 2 may include a fluid delivery conduit 30 in fluid communication with an interior chamber 34 in which coolant may expand. The interior chamber 34 may be in thermal communication with a treatment electrode 50 at the distal tip 62 that is composed of a thermally conductive material (for example, a metal), such that expansion of the coolant cools the treatment electrode 50 to a temperature sufficient to cool tissue to ablation or sub-ablation temperatures. As with the device of FIG. 1, coolant flow into the interior chamber 34 may be controlled, either automatically or manually, by the control unit 14. For example, the coolant flow may be according to a duty cycle algorithm.

Referring now to FIG. 3, a graphical representation of an exemplary cryoablation system duty cycle 64 is shown. In general, the duty cycle 64 (or "duty-controlled cycle") presents a freeze-warm-freeze cycle that more efficiently creates tissue lesions than a single, longer freeze cycle. The duty cycle 64 may include any number of consecutive freeze cycles 68 and warm cycles 70 necessary to create a desired lesion in the target tissue (for example, myocardial tissue). The duty cycle 64 may be controlled either manually by the user with one or more user input devices (which may include a computer 58) or automatically by the control unit 14 or component thereof. For example, the duty cycle 64 may be controlled by programming a computer 58 or processor including one or more algorithms to automatically operate the system 10 according to a predetermined duty cycle 64, or by a computer 58 or processor including one or more algorithms to automatically control the system 10 generally based on a predetermined duty cycle 64 but adjusted in response to one or more feedback signals. Further, one or more parameters of the duty cycle 64 may be shown on one or more displays or screens 60 for monitoring, controlling and/or modifying the duty cycle 64 as necessary.

As described above, the system 10 may be a continuous flow system instead of a fixed initial volume system. In order to adjust the temperature of the one or more treatment elements (for example, to transition between a freeze cycle 68 and a warm cycle 70), the flow rate of the fluid within the fluid flow path of the system 10 may be adjusted upstream and/or downstream of the device 12. This adjustment in flow rate will consequently adjust the temperature of a treatment element of the device 12. For example, flow rates may be adjusted using one or more pressure transducers controlling fluid injection pressure in the fluid delivery conduit 30 and controlling vacuum pressure in the fluid exhaust conduit 38 (not shown).

The duty cycle 64 may include one or more freeze or ablation cycles 68 and one or more thaw or maintenance cycles 70. Several freeze and warm cycles 68, 70 are shown in FIG. 3. In general, an exemplary duty cycle 66 is graphically expressed in FIG. 3 in terms of both temperature (line 72) and flow rate (line 74). The y-axis of the graph represents temperature (T), and y-axis of the graph represents time (t). Although specific flow rates are not expressly shown on the y-axis of the graph, the approximate flow rate (F) is shown adjacent the flow rate line 74 at each time interval ($t_1$, $t_2$, $t_3$, $t_4$, $t_5$, etc.). As is shown in FIG. 3, the duty cycle 64 may include pulsatile coolant flow, such that flow rate and therefore temperature may fluctuate many times over the course of a duty cycle 64. Further, temperature and flow rate may be inversely related, such that temperature increases as flow rate decreases and vice versa. In general, the greater the flow rate of the coolant within an interior chamber 34 proximate a treatment element, the greater the amount of heat that may be removed from tissue adjacent the treatment element.

The freeze cycle 68 of the exemplary duty cycle 64 shown in FIG. 3 may be a freeze cycle 68 of a cryoablation treatment (such as shown in time interval $t_1$). As such, the initial temperature of the first freeze cycle 68 may be between approximately 37° C. and room temperature. However, in freeze cycles 68 occurring after warm cycles 70, this initial temperature may be much lower. As shown in FIG. 3, a freeze cycle 68 may occur, for example, in each of time intervals $t_1$, $t_3$, and $t_5$. Likewise, a warm cycle 70 may occur, for example, in each of time intervals $t_2$ and $t_4$. Additionally, although not shown, a final warm cycle in which the ice ball is allowed to completely thaw may occur in a time interval after the cryotreatment procedure is completed.

Coolant flow within the freeze cycle 68 may be referred to as "ablation flow" (which appears as a "hill" in the graph), and the temperature of the treatment element within the freeze cycle 68 may be referred to as "ablation temperature." Likewise, coolant flow within the warm cycle 70 may be referred to as "maintenance flow" (which appears as a "valley" in the graph), and the temperature of the treatment element within the warm cycle 70 may be referred to as "maintenance temperature." Flow rate and temperature may be adjusted many times within a single freeze or warm cycle 68, 70 in order to optimize lesion creation. Additionally or alternatively, the time interval of a freeze or warm cycle 68, 70 may be adjusted for the same reason. As a non-limiting example, such adjustments may be based on changes in tissue biophysical properties detected by one or more system sensors. Further, although not shown, the coolant temperature may be monitored using, for example, surface thermocouples or by measurement of the coolant temperature after it has expanded (for example, proximal the interior chamber 34 of a cryoballoon 32, within the fluid return lumen). In general, however, the average ablation flow may be sufficient to produce treatment element temperatures within a range that cause disruption or destruction of tissue (i.e. tissue ablation), which may be a permanent effect. Further, the average maintenance flow may be sufficient to produce treatment element temperatures within a range that allows the treatment element and adjacent tissue to warm above ablation temperatures, but within a range that does not break cryoadhesion between the treatment element and tissue (that is, does not allow the ice ball to completely thaw).

Continuing to refer to the exemplary duty cycle 64 of FIG. 3, during time interval $t_1$, a freeze cycle 68, the flow rate of the coolant (for example, as it is injected into an interior chamber 34 of a cryoballoon) may increase to between approximately 7000 and 7500 standard cubic centimeters per minute (sccm) (e.g., approximately 7200 sccm). Consequently, the temperature of the treatment element may decrease to between approximately −50° C. to approximately −70° C. (e.g., approximately −70° C.). During time interval $t_2$, a warm cycle 70, the flow rate of the coolant may decrease to between approximately 3500 sccm and approximately 3000 sccm (e.g., approximately 3000 sccm), and the temperature of the treatment element may increase to between approximately −15° C. and approximately −5° C. (e.g., approximately −5° C.). During time interval $t_3$, a freeze cycle 68, the flow rate of the coolant may increase to between approximately 4500 sccm to approximately 5000 sccm (e.g., approximately 5000 sccm), and the temperature of the treatment element may decrease to between approximately −35° C. to approximately −40° C. (e.g., approximately −40° C.). During time interval $t_4$, a warm cycle 70, the flow rate may decrease to between approximately 4000 sccm and approximately 4200 sccm (e.g., approximately 4000 sccm), and the temperature of the treatment element may increase to between approximately −15° C. and approximately −20° C. (e.g., approximately −20° C.). During time interval $t_5$, a freeze cycle 68, the flow rate of the coolant may increase to approximately 4500 sccm, and the temperature of the treatment element may decrease to approximately −30° C.

Even though flow rates are shown in FIG. 3, the flow rate during any warm cycle 70 may be reduced to zero temporarily, as long as the temperature of the treatment element is not allowed to reach temperatures at which cryoadhesion would be broken.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of creating a lesion in tissue, the method comprising:
   positioning a distal end of a medical device proximate an area of target tissue; and
   operating a control unit according to a treatment cycle, the treatment cycle including:
      supplying coolant to the distal portion of the medical device at a first flow rate, the first flow rate causing the distal portion of the medical device to reach a first temperature;
      supplying coolant to the distal portion of the medical device at a second flow rate, the second flow rate causing the distal portion of the medical device to reach a second temperature, the second temperature being higher than the first temperature and the second flow rate being lower than the first flow rate; and
      supplying coolant to the distal portion of the medical device at a third flow rate, the third flow rate causing the distal portion of the medical device to reach a third temperature, the third temperature being lower than the second temperature, and the third flow rate being lower than the first flow rate but higher than the second flow rate,
   the first and third temperatures being sufficiently low so as to ablate the target tissue and cause cryoadhesion between the distal portion of the medical device and the target tissue, the second temperature being above a temperature at which ablation occurs and below a temperature at which cryoadhesion is broken.

2. The method of claim 1, wherein the treatment cycle further comprises:
supplying coolant to the distal portion of the medical device at a fourth flow rate, the fourth flow rate causing the distal portion of the medical device to reach a fourth temperature, the fourth temperature being higher than the first and third temperatures but lower than the second temperature, and the fourth flow rate being higher than the second flow rate but lower than the first and third flow rates,
the fourth temperature being above a temperature at which ablation occurs and below a temperature at which cryoadhesion is broken.

3. The method of claim 1, wherein the distal portion of the medical device includes an inflatable balloon defining an interior chamber in communication with a fluid supply.

4. The method of claim 3, wherein the fluid supply continuously delivers coolant to the interior chamber both during inflation of the balloon and during the treatment cycle.

5. The method of claim 1, wherein the distal portion of the medical device has a fixed diameter and defines an interior chamber in communication with a fluid supply.

6. The method of claim 5, wherein the fluid supply continuously delivers coolant to the interior chamber during the treatment cycle.

7. The method of claim 1, wherein the first temperature is between approximately −50° C. to approximately −70° C.

8. The method of claim 7, wherein the first flow rate is between approximately 7000 and 7500 sccm.

9. The method of claim 8, wherein the second temperature is between approximately −15° C. and approximately −5° C.

10. The method of claim 9, wherein the second flow rate is between approximately 3500 sccm and approximately 3000 sccm.

11. The method of claim 2, wherein the third temperature is between approximately −35° C. to approximately −40° C.

12. The method of claim 11, wherein the third flow rate is between approximately 4500 sccm to approximately 5000 sccm.

13. The method of claim 12, wherein the fourth temperature is between approximately −15° C. and approximately −20° C.

14. The method of claim 13, wherein the fourth flow rate is between approximately 4000 sccm and approximately 4200 sccm.

15. A method of ablating tissue, the method comprising:
positioning a treatment element coupled to the distal end of a medical device proximate an area of target tissue; and
operating a control unit in accordance with a duty cycle, the control unit being in communication with the treatment element, the duty cycle including a plurality of freeze-warm cycles, each freeze-warm cycle including:
supplying coolant to the treatment element at a first flow rate, the first flow rate causing the treatment element to reach a first temperature, the first temperature causing ablation of the target tissue and causing cryoadhesion between the treatment element and target tissue; and
supplying coolant to the treatment element at a second flow rate, the second flow rate causing the treatment element to reach a second temperature, the second temperature being higher than the first temperature and the second flow rate being lower than the first flow rate, the second temperature being above a temperature at which ablation occurs and below a temperature at which cryoadhesion is broken.

16. The method of claim 15, wherein the duty cycle includes two or more freeze-warm cycles.

17. A system for ablating tissue, the system comprising:
a medical device including a distal portion defining a treatment element;
a fluid supply in communication with the treatment element, the fluid supply continuously delivering fluid to the treatment element when the treatment element is activated; and
a control unit having a processor, the processor operating to control the flow of fluid according to a duty cycle, the duty cycle including:
a freezing cycle over a first time interval during which the fluid flow rate is increased to lower the temperature of the treatment element to a first ablation temperature at which cryoadhesion takes place;
a warming cycle over a second time interval during which the fluid flow rate is decreased to raise the temperature of the treatment element to a first maintenance temperature that is below a temperature at which cryoadhesion is broken, the first maintenance temperature being higher than the first ablation temperature;
a freezing cycle over a third time interval during which the fluid flow rate is increased to lower the temperature of the treatment element to a second ablation temperature at which cryoadhesion is continued, the second ablation temperature being higher than the first ablation temperature but lower than the first maintenance temperature; and
a warming cycle over a fourth time interval during which the fluid flow rate is decreased to raise the temperature of the treatment element to a second maintenance temperature, the second maintenance temperature being higher than the first ablation temperature but lower than the first maintenance temperature, the second maintenance temperature being below the temperature at which cryoadhesion is broken.

18. The system of claim 17, wherein the first ablation temperature is between approximately −50° C. to approximately −70° C. and the first flow rate is between approximately 7000 and 7500 sccm.

19. The system of claim 18, wherein the first maintenance temperature is between approximately −15° C. and approximately −5° C. and the first maintenance flow rate is between approximately 3500 sccm and approximately 3000 sccm.

20. The system of claim 19, wherein the second ablation temperature is between approximately −35° C. to approximately −40° C. and the second ablation flow rate is between approximately 4500 sccm to approximately 5000 sccm.

21. The system of claim 20, wherein the second maintenance temperature is between approximately −15° C. and approximately −20° C. and the second maintenance flow rate is between approximately 4000 sccm and approximately 4200 sccm.

* * * * *